(12) United States Patent
Aase

(10) Patent No.: US 11,971,382 B2
(45) Date of Patent: Apr. 30, 2024

(54) SYSTEM FOR MEASURING THE COMPOSITION OF A MULTI-PHASE FLOW IN A PIPE BY ANALYZING ELECTRICAL CHARACTERISTICS

(71) Applicant: Roxar Flow Measurement AS, Stavanger (NO)

(72) Inventor: Frode Hugo Aase, Stord (NO)

(73) Assignee: ROXAR FLOW MEASUREMENT AS, Stavanger (NO)

( * ) Notice: Subject to any disclaimer, the term of this patent is extended or adjusted under 35 U.S.C. 154(b) by 388 days.

(21) Appl. No.: 17/285,406

(22) PCT Filed: Oct. 25, 2019

(86) PCT No.: PCT/EP2019/079232
§ 371 (c)(1),
(2) Date: Apr. 14, 2021

(87) PCT Pub. No.: WO2020/084132
PCT Pub. Date: Apr. 30, 2020

(65) Prior Publication Data
US 2021/0396700 A1    Dec. 23, 2021

(30) Foreign Application Priority Data
Oct. 26, 2018 (NO) .................................. 20181382

(51) Int. Cl.
*G01N 27/22* (2006.01)
*G01F 1/74* (2006.01)
(Continued)

(52) U.S. Cl.
CPC ............ *G01N 27/221* (2013.01); *G01F 1/74* (2013.01); *G01N 27/08* (2013.01); *G01N 33/2823* (2013.01)

(58) Field of Classification Search
None
See application file for complete search history.

(56) References Cited

U.S. PATENT DOCUMENTS

| 4,751,842 A | 6/1988 | Ekrann et al. |
| 5,287,752 A * | 2/1994 | Den Boer ............... G01F 1/712 73/861.04 |

(Continued)

FOREIGN PATENT DOCUMENTS

| NO | 307393 B1 | 3/2000 |
| NO | 340852 B1 | 6/2017 |
| WO | WO-2007009097 A1 | 1/2007 |

OTHER PUBLICATIONS

Klein, Marc-Oliver; International Search Report; PCT/EP2019/079232; dated Jan. 15, 2020; 5 pages.

(Continued)

*Primary Examiner* — Jas A Sanghera
(74) *Attorney, Agent, or Firm* — Bradley Arant Boult Cummings

(57) ABSTRACT

System for measuring the composition of a multiphase fluid flow in a pipe, the multiphase flow containing a mixture of gas and liquid. The system comprising a first and a second sensor arrangement, wherein each sensor arrangement is adapted to measuring electrical characteristics (i.e. impedance) of the flow at a predetermined rate. The system also including an analysis unit being adapted to monitor the measured electrical characteristics from said first and second sensor arrangement and to detect occurrences of time periods involving a predetermined relationship between the measured characteristics, and during these periods assuming a liquid rich phase and calculating the composition based on the electrical characteristics.

8 Claims, 2 Drawing Sheets

(51) Int. Cl.
*G01N 27/08* (2006.01)
*G01N 33/28* (2006.01)

(56) References Cited

U.S. PATENT DOCUMENTS

| | | |
|---|---|---|
| 5,719,340 A | 2/1998 | Poortmann et al. |
| 5,929,342 A | 7/1999 | Thompson |
| 2013/0144548 A1* | 6/2013 | Xie ........................ G01R 27/00 |
| | | 702/65 |

OTHER PUBLICATIONS

Thorn, R., et al.; "Three-phase flow measurement in the petroleum industry"; Meas. Sci. Technol. 24 (2013) 012003; Oct. 29, 2012; 17 pages.

\* cited by examiner

SYSTEM FOR MEASURING THE COMPOSITION OF A MULTI-PHASE FLOW IN A PIPE BY ANALYZING ELECTRICAL CHARACTERISTICS

The present invention relates to a flow measuring system for measuring compositions in multiphase fluid flow in a pipe, especially measuring composition and flow rates in a fluid mixture of gas, water and oil in hydrocarbon production installations.

It is well known that in hydrocarbon production there is need to monitor the composition of the produced fluids. This is often done by measuring permittivity of the flow using electrodes, possibly in combination with density measurements using gamma radiation and differential pressure measurements. It is also known that with a certain gas content the liquid phase in the flow may occur as liquid slugs moving in the flow. As is shown in NO307393 this may be used to measure the content of the liquid part, such as the water liquid ratio (WLR) of the liquid. In NO307393 this is performed by detecting the time periods where the permittivity of the flow is high and measure the permittivity in those periods when the slugs pass the electrodes.

As is explained in NO307393, these periods of high permittivity are assumed to be mainly liquid, however, may still contain a small amount of gas. It is further explained that the process of finding a virtually gas free liquid sample can be optimized by using electrodes mainly sensitive to the flow along the periphery of the pipe, and that it can be further optimized by a calibration factor for remaining gas.

One limitation with the solution described in NO307393 is the fact that the electric field distribution within the sensing volume is a so-called soft-field, meaning that the electric field distribution will depend also on the permittivity of the flow outside the sensing volume. The measurements made by the local field electrodes proposed in NO307393 for measuring along the periphery of the pipe, may thus be distorted by what is in the center of the pipe. Additionally, the measurement will be influenced by the axial flow distribution. Ideally the determination of water cut should therefore be based only on measurements performed when there is a homogeneous distribution over the full cross-section, and also when this is fulfilled for a certain distance, e.g. a few pipe diameters distance before and after the electrode section.

Also, the solution in NO307393 as well as a related solution discussed in WO2007/009097 any changes over a certain threshold is measured, which makes it difficult to distinguish between homogeneous and inhomogeneous flow conditions.

NO340852 shows how the method and system described in NO307393 can be extended with an additional axially spaced electrode plane, enabling cross correlation for velocity measurement, and how this can be combined for measuring multiphase flowrates in a slugging flow. NO340852 discusses the above-mentioned limitation of NO307393, but does not propose an alternative solution.

It is an objective of the present invention is to improve the measurements during the slug periods. This is obtained as presented in the accompanying claims.

The present invention thus uses two sets of sensor arrangements such as electrical impedance sensors at different locations along the length of the pipe or along the circumference in one position in the pipe. For the purpose of this invention it is not important what kind of electrical impedance sensors are used, e.g. they could be either capacitance or conductance sensors, or microwave sensors, or combinations thereof. It will however be a criteria that the two sensors respond similar each other when the flow is homogeneous, and different to each other when the flow is in-homogeneously distributed.

The invention will in the following be explained based on impedance sensors similar to those described in NO 307393 and NO340852, i.e. measuring low frequency electrical impedance between predetermined sets of surface plate electrodes in the periphery of the pipe. The sensors thus configured for measuring capacitance when the flow is predominantly non-conducting (typically oil-continuous liquid phase) and measuring conductance when the flow is conducting (typically water-continuous liquid phase). The measured capacitance or conductance are respectively converted to permittivity or conductivity through per se known methods. Preferably the two sensors are calibrated to measure equal permittivity (or conductivity) for a homogeneously distributed flow, the configuration of the two sensors is however selected such that they have different sensitivity fields, thus responding differently to an inhomogeneous distribution within their respective sensing regions. The measurements at the two locations are then compared and the relationship between the measured values are used to provide measurements of the fluid flow under certain conditions.

The present invention will be discussed more in detail below with reference to the accompanying drawings, illustrating the invention by way of examples.

Figure 1A:
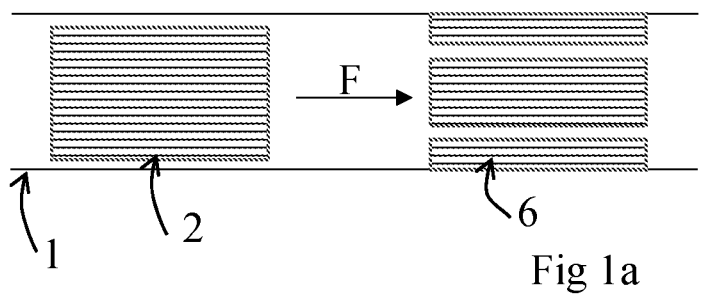
FIG. 1a,1b illustrates the sensors used according to the invention.

The invention is in the following described for oil-continuous flow F in a pipe 1 as illustrated in FIG. 1a, using the sensor arrangements 2,6 and associated electronics (not shown) for measuring capacitance and then converting to permittivity in a calculation unit. However, the invention could equally well have been explained for use in water-continuous flow by the corresponding measurement of conductance and converting to conductivity.

Figure 1B:
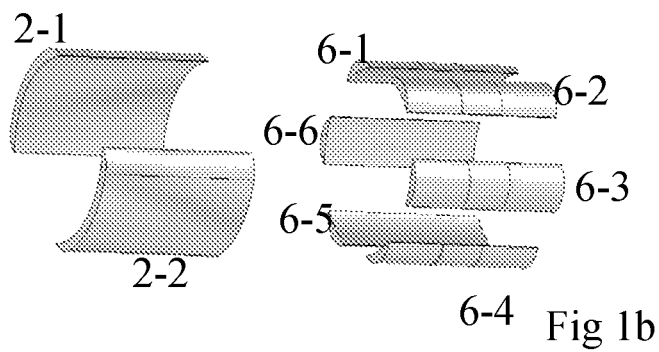

In a first embodiment the present invention may be described by two differently configured sensor arrangements 2,6, spaced axially a predetermined distance along the pipe, typically in the range 0.01 to 0.5 meters, preferably in the range 0.05 to 0.2 meters center to center, the delay between the occurrence of similar measurements at the two locations thus depending on the flow rate and the distance. In the example of FIGS. 1a and 1b, the upstream electrode plane of the first sensor arrangement 2 consists of two diametrically oriented electrodes 2-1,2-2, each preferably spanning around 90 degrees of the periphery of the pipe 1. The downstream electrode plane of the second sensor arrangement 6 in this example consists of six electrodes 6-1 . . . 6-6 evenly distributed around the circumference of the pipe 1. This electrode configuration is known from a commercially available instrument by Roxar (MPFM 2600) e.g. as illustrated in FIG. 5 in R Thorn et al: "Three-phase flow measurement in the petroleum industry" Measurement Science and Technology•October 2012 Meas. Sci. Technol. 24 012003, and is not part of the present invention. The present invention is related to and suitable for the use of configurations like this for determining WLR in a slugging flow, as will be explained below.

Figure 2A:
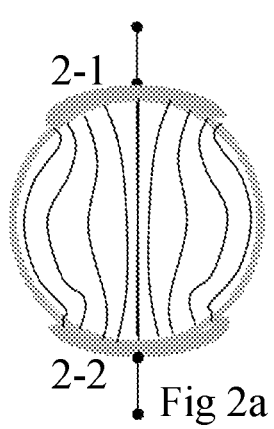
FIG. 2a,2b illustrates the electrical field between the electrodes in the sensors.
Figure 2B:
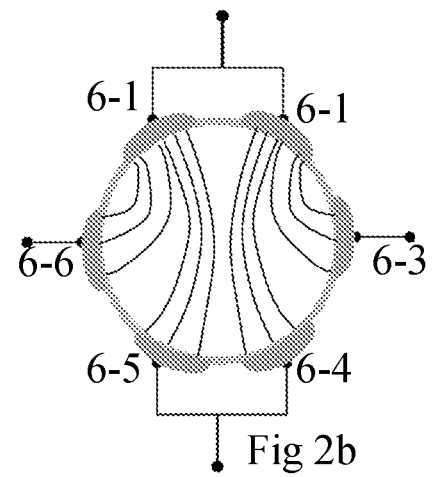

In the illustrated example the invention will be explained by denoting the two-electrode plane 2 as Channel 2. For the six-electrode plane 6 d two adjacent electrodes 6-1,6-2 as excitation electrodes, and the two diametrically positioned electrodes 6-4,6-5 as parallel coupled measurement electrodes. This may be denoted as Channel 1. The two remaining electrodes 6-3,6-6 can be floating, or preferably kept at a known potential, e.g. the same as the measurement electrodes. The electrical field lines are in this case shown in FIG. 2a for channel 2 and FIG. 2b for channel 1, when assuming a homogeneous fluid in the pipe.

In addition to the two plus six electrode configuration of course other constellations maybe contemplated depending on the available technology and required measurements, including two plus two, two plus four, six plus six, etc. Odd numbers such as two plus three and three plus five may also be contemplated depending on the available switching and measuring technology. Non-symmetric distributions of electrodes will have the effect of different radial sensitivity distribution of the electrical field, which may also be contemplated in some cases.

Being sensitive to different locations of the flow these two measurement channels will respond differently to a non-homogeneous distribution as the turbulent flow will not have similar characteristics in different locations over any period of time, Ideally they will however measure the same permittivity when the fluid in their respective sensing regions is homogeneous, and if it at the same time has equal fractional composition. This is utilized by calculating the ratio between the measurement in the two channels, and in that way the following considerations can be made:

- Homogenous flow, but with unequal fractions, will result in a ratio different than 1. This is typical for head or tail of a liquid slug.
- Non-homogenous flow, and with non-symmetrical radial distribution, will also result in a ratio different than 1, even if equal fractions in the two planes (due to the difference in radial sensitivity). This is typical for churn type flow.
- A value close to 1 thus characterize a section of the flow which is homogeneous not only in radial direction, but also for a certain length in axial direction. This is typical for liquid dense bubbly flow as well as for mist flow.
- Annular flow can also result in a ratio close to 1. Annular flow can be expected for very high gas fractions in the cross section, typically well above 95%.
- The liquid dense bubbly samples can easily be discriminated from the annular and mist flow samples by their difference in absolute permittivity.
- High permittivity samples, which at the same time have a ratio close to 1 between the two differently configured measurement channels therefore means a liquid dense section of the flow which is homogeneous not only in radial direction, but also for a certain length in axial direction. This is typical for the mid-section of a liquid slug in slugging flow.

The following measurement and evaluation steps can now be implemented in an automated measurement procedure:
1. Measure a continuous stream of permittivity (or conductivity) values from the two axially distributed sensors (channels 1 and 2).
2. Calculate the ratio between the two measurements for each time step, either continuously, or over a given time period.
3. Select all measurements within a defined time window (from seconds to several minutes, or even hours) with a ratio close to 1 into a 'homogeneous sample' register.
4. Select the x % (typically 0.1%) highest permittivity (or conductivity) measurements from this register, representing a virtual liquid sample.
5. Calculate the average permittivity (or conductivity) for the virtual liquid sample.
6. Calculate WLR for the virtual liquid sample, assuming zero (or a fixed low value) gas in this 'virtual liquid' sample.

Figure 3A:
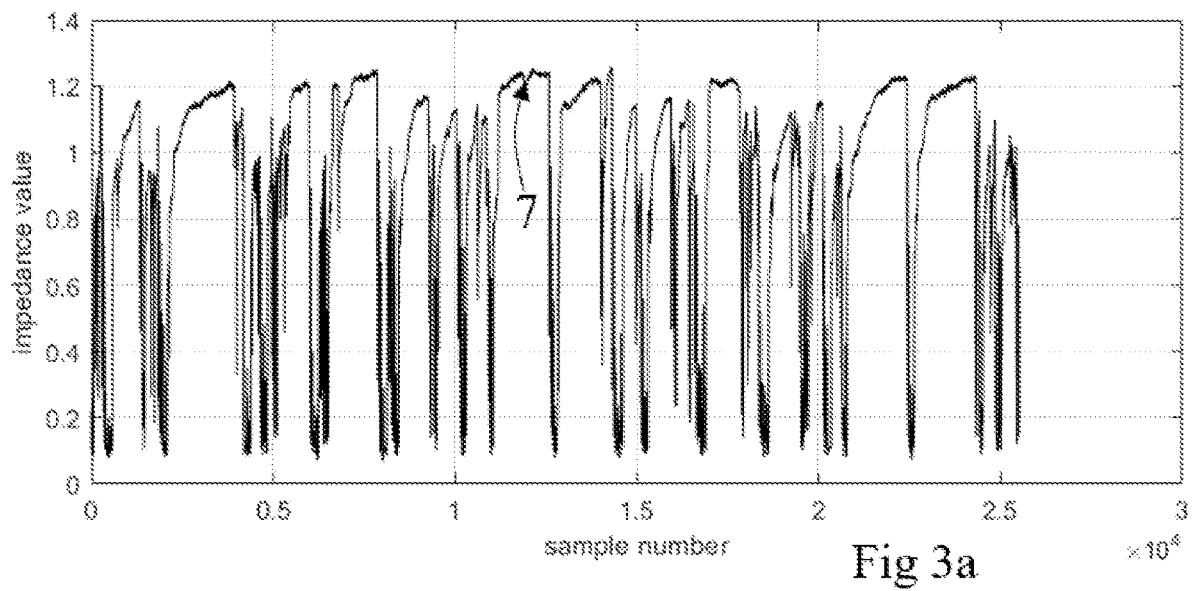
FIG. 3a,3b illustrates the measurements made by one of the sensors.

FIG. 3a is a plot of chronological 'homogeneous' samples collected according to step 3 of the procedure above including one fairly stable period 7 possibly indicating a slug or continuous period with high conductivity liquid. According the invention at least one such stable period is measured by each channel confirming it as a stable feature in the flow. The occurrence at the two channels may either be shifted in time depending on the flow rate if the channels are in separate positions along the flow or occur simultaneously if the channels are measured in the same plane.

Figure 3B:
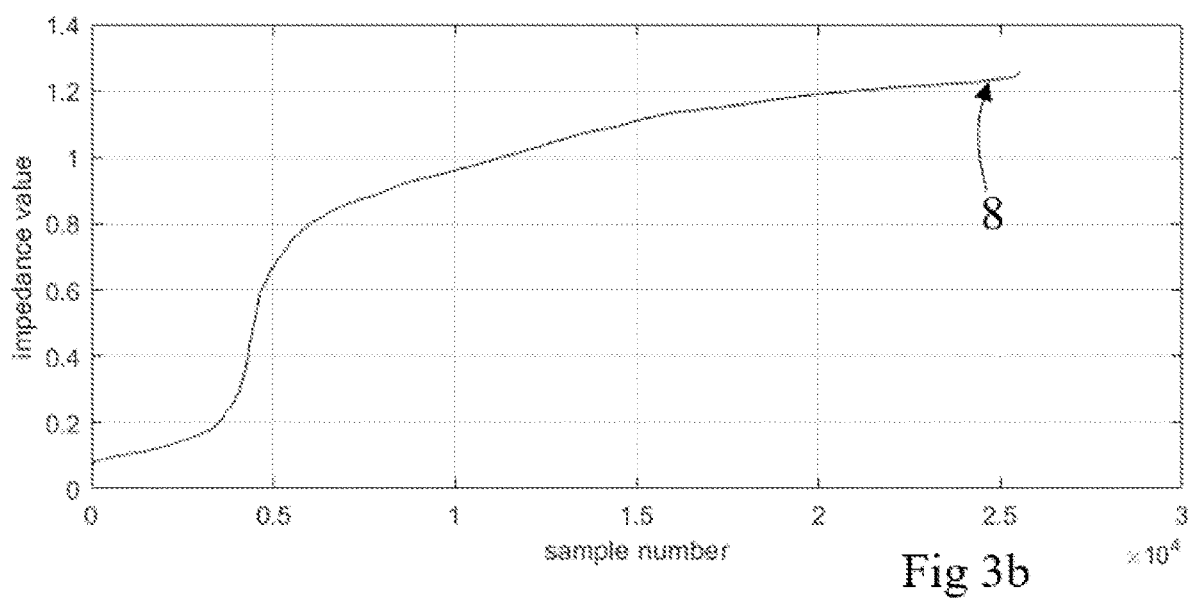

In FIG. 3b the same samples are sorted according to their permittivity value, and only the samples to the far right 8 may be considered to represent 'virtual liquid samples', ref step 4 of the procedure. The x % may be predetermined, e.g. 0.1% as indicated above, based on known flow characteristics or be estimated based on a measured variation during the time window being within predetermined limits. The duration of the time window may depend on the flow conditions, but should be sufficient to avoid very short incidents, e.g. from measuring errors or short changes not long enough to distinguish between homogeneous and inhomogeneous flow conditions.

The duration of the time window 7 in embodiments using two electrode planes, as shown in the FIGS. 1 and 2, may be less than the time required for the flow to pass both electrode planes as long as the presence of such feature is recognized as the same in both cases.

The quality of the method as described will to a large extent depend on the assumption of close to zero gas in step 6 above. The method is therefore most suitable in a slugging flow, and the use of the method should be combined with criteria for determining slug flow, and/or other suitable measures, such as in situ verification, for determining the validity of the method. There are several formulas for converting the measured permittivity to WLR, e.g. such as described in NO307393 and NO340852.

As mentioned above it will be understood that the method described here can also use other electrode configurations than the one shown in FIG. 1, as long as the two sensors fulfill the criteria that the two sensors respond similar to each other when the flow is homogeneous, and different to each other when the flow is in-homogeneously distributed. Even the configuration in FIG. 1 can be used differently, e.g. by measuring between only two adjacent electrodes in the six-electrode plane, or by any other configuration between the electrodes made possible by the measurement electronics.

The electrodes in the different channels may be calibrated using a known fluid flow so as to make sure the ratio between the measurements is 1:1 when a homogenous flow with the same content passes the channel electrodes. This may especially be necessary when two different configurations are used in the two channels, as in the abovementioned examples referring to FIGS. 1 and 2, but may also be used in case contaminations or similar on the sensors may affect the measurements. Ratio other than the preferred 1:1 could also result from variations in the individual calibration between the sensors, as well as changes in calculation methods. As an alternative to the calibration for obtaining a 1:1 ratio, the predetermined ratio may be changed into any ratio between the channels representing the same fluid characteristics with the difference in electrode setup.

Other calculations may also be applied to any such measurement that have similar sensitivity to homogenous flow and different sensitivity to in-homogenous flow and achieving the same objective of finding homogeneous samples. As example, by calculating the delta (or difference) between the channels (CH1-CH2) rather than the ratio, the homogenous periods would give close to zero, hence achieving the same as using ratios. A third methodology would be to monitor the linear gain value between two samples in time (i.e: sample current time from channel 1 and a 100 msec delayed sample from channel 2) over time. When the gain value is low (i.e.: close to zero) for a period of time the measurements in the samples are similar, which implies that both sensors are seeing a homogenous like fluid for that period, and hence achieving the same as using the ratio 1:1.

In a simplified version of the present invention, the 6-step procedure above can also be used on one single plane sensor, e.g. the six-electrode plane 6-1, . . . , 6-6, but now using two different electrode configurations of the same plane as channels 1 and 2 in step 1. This modified use of the method will find radially homogeneous samples, but increased uncertainty in the determination of WLR must be expected as axial variations in the flow direction will not be filtered out. Additional filtering may then be applied, e.g. allowing only a certain part of a sufficiently long period of accepted ratio into the register of step 3.

In this embodiment the electrode pairs or sets may possibly be dynamically changed in a sequence measuring different subsets of the pipe cross section. As an example, a liquid slug large enough to dominate two sets of electrode pairs may be sufficient to provide a measure during a time window of the characteristics of that slug.

To summarize the present invention relates to a system for measuring the compositions in multiphase fluid flow in a pipe, especially measuring composition and flow rates in a fluid mixture of gas, water and oil, e.g. liquid ratio in multiphase fluid flow in a pipe where the multiphase flow contains a mixture of gas and liquid such as gas and oil or water. The system comprising a first and a second sensor arrangement, wherein each sensor arrangement is adapted to measuring electrical characteristics of the flow at a predetermined rate where the two sensors are configured to respond differently to inhomogeneous flow composition but similar to homogeneous flow composition. The system also includes an analysis unit being adapted to monitor the measured electrical characteristics from said first and second sensor arrangement and to detect occurrences of time periods involving a predetermined relationship between the measured characteristics in said sensor arrangements, and during these periods assuming a homogeneous phase, e.g. constituted by a liquid slug or gas bobble in the pipe and calculating the composition, such as the water/liquid ratio, based on the electrical characteristics.

In addition to using the relationship between the measured characteristics the analysis unit may be adapted to select the time periods with samples having a certain impedance, conductivity or capacitance values, such as the highest impedance, as well as the predetermined relationship between the sensor arrangements in the monitored sequence for calculating the composition of the flow The predetermined relationship may be defined as essentially 1:1 ratio or zero difference between the measured characteristics as well as the linear gain value between two samples in time, but other ratios or differences may also be considered depending on constructional differences between the sensor arrangements and calibration factors.

The sensor arrangements may be configured in several different ways, for example four electrodes may be spaced around the pipe in the same axial position, being to be configured as said first and second sensor arrangements, or the first and a second sensor arrangement may be located at different positions along the pipe with a predetermined distance between them, where the analysis unit may take into account the time delay between the measurements related to the flow velocity.

The first and second sensor arrangements may be constituted by several constellations of electrodes measuring the characteristics over the complete cross section of the flow or parts of the cross section If the first and second sensor arrangements are positioned in different locations along the pipe the distance and flow velocity may be used to compensate for the different arrival times of the flow features. The velocity measuring means may be constituted by correlation measurements as is well known within the field, differential pressure or other flow velocity measurements. The analysis unit may then be provided with the flow velocity and compensate for the time differences between the samples made at different positions along the pipe, something that might be important if the periods within the predetermined relationships are short.

The invention claimed is:

1. A system for measuring the composition of a multiphase fluid flow in a pipe, the multiphase flow containing a mixture of gas and liquid, the system comprising:
   a first and a second sensor arrangement, each including at least two electrodes positioned in the pipe, wherein each sensor arrangement is adapted to measuring electrical impedance of the flow at a predetermined rate wherein the two sensor arrangements are configured to have different sensitivity fields, thus responding differently to an inhomogeneous distribution within their respective sensing regions but similar to homogeneous flow composition; and
   an analysis unit adapted to:
      monitor the measured electrical impedance from the first and second sensor arrangement;
      calculate the ratio between the two measurements for each time step;
      select all measurements within a defined time window in each of the measurements with a ratio being essentially 1:1;
      detect measurements of the selected measurements with the highest impedance at both sensor arrangements representing a virtual liquid sample with low gas content; and
      calculate the composition based on the detected highest-impedance measurements, thus providing a measure of the water liquid ratio (WLR) in the virtual liquid sample.

2. The system according to claim 1, wherein the first and second sensor arrangement is positioned in the same axial position along the pipe.

3. The system according to claim 2, wherein at least one of the sensor arrangements comprises at least three electrodes adapted to measure the electrical impedance in at least two different parts of the cross section of the flow.

4. The system according to claim 2, wherein a first of the sensor arrangements comprises two electrodes measuring the electrical impedance of the fluid flow and a second of the sensor arrangements comprises at least three electrodes adapted to measure the electrical impedance in at least two different parts of the cross section of the flow.

5. The system according to claim 1, wherein the first and a second sensor arrangement are located at different positions along the pipe with a predetermined distance between them.

6. The system according to claim 5, including means for measuring the flow velocity, and wherein the analysis unit is provided with the flow velocity, and is adapted to compensate for the time differences between the samples made at different positions along the pipe.

7. The system according to claim 1, wherein the measurements from each sensor arrangement is calibrated so as to give the same signal when representing the same fluid characteristics.

8. A system for measuring the composition of a multiphase fluid flow in a pipe, the multiphase flow containing a mixture of gas and liquid, the system comprising:
 a first and a second sensor arrangement, each including at least two electrodes positioned in the pipe, wherein each sensor arrangement is adapted to measuring electrical impedance of the flow at a predetermined rate wherein the two sensor arrangements are configured to have different sensitivity fields, thus responding differently to an inhomogeneous distribution within their respective sensing regions but similar to homogeneous flow composition; and
 an analysis unit adapted to:
  monitor the measured electrical impedance from the first and second sensor arrangement;
  calculate the ratio between the two measurements for each time step;
  select all measurements within a defined time window in each of the measurements with a predetermined ratio between them representing the same fluid characteristics in both sensors;
  detect measurements of the selected measurements with the highest impedance at both sensor arrangements representing a virtual liquid sample with low gas content; and
  calculate the composition based on the detected highest-impedance measurements, thus providing a measure of the water liquid ratio (WLR) in the virtual liquid sample.

\* \* \* \* \*